(12) United States Patent
Garwood et al.

(10) Patent No.: US 7,403,006 B2
(45) Date of Patent: *Jul. 22, 2008

(54) FREQUENCY SWEPT EXCITATION FOR MAGNETIC RESONANCE

(75) Inventors: Michael Garwood, Medina, MN (US); Djaudat S. Idiyatullin, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 29 days.

This patent is subject to a terminal disclaimer.

(21) Appl. No.: 11/548,664

(22) Filed: Oct. 11, 2006

(65) Prior Publication Data

US 2007/0188171 A1 Aug. 16, 2007

Related U.S. Application Data

(60) Provisional application No. 60/725,361, filed on Oct. 11, 2005.

(51) Int. Cl.
*G01V 3/00* (2006.01)

(52) U.S. Cl. ........................... 324/310; 324/307

(58) Field of Classification Search ......... 324/300–322; 600/410–435
See application file for complete search history.

(56) References Cited

U.S. PATENT DOCUMENTS

| | | | | |
|---|---|---|---|---|
| 3,968,424 A * | 7/1976 | Ernst | ........................ | 324/310 |
| 3,975,675 A | 8/1976 | Dunand et al. | | |
| 4,209,843 A * | 6/1980 | Hyatt | ........................ | 708/422 |
| 4,553,213 A * | 11/1985 | Hyatt | ........................ | 332/185 |
| 4,553,221 A * | 11/1985 | Hyatt | ........................ | 708/308 |
| 4,581,715 A * | 4/1986 | Hyatt | ........................ | 708/403 |
| 4,602,641 A | 7/1986 | Feinberg | | |
| 4,658,252 A * | 4/1987 | Rowe | ........................ | 340/5.63 |
| 4,686,655 A * | 8/1987 | Hyatt | ........................ | 367/59 |
| 4,944,036 A * | 7/1990 | Hyatt | ........................ | 367/43 |
| 5,053,983 A * | 10/1991 | Hyatt | ........................ | 708/306 |
| 5,248,882 A * | 9/1993 | Liang | ........................ | 250/291 |
| 5,869,959 A * | 2/1999 | Tomikawa | ................ | 324/76.27 |
| 6,201,392 B1 * | 3/2001 | Anderson et al. | ............ | 324/300 |
| 6,392,408 B1 * | 5/2002 | Barrall et al. | ................ | 324/300 |

(Continued)

FOREIGN PATENT DOCUMENTS

WO  WO 96/10193  4/1996

OTHER PUBLICATIONS

Idiyatullin et al., "Fast and quiet MRI using a swept radiofrequency", *Journal of Magnetic Resonance*, Academic Press, Orlando, FL., vol. 181, No. 2, Aug. 2006, pp. 342-349, XP005569620 ISSN: 1090-7807.

(Continued)

*Primary Examiner*—Brij B. Shrivastav
*Assistant Examiner*—Dixomara Vargas
(74) *Attorney, Agent, or Firm*—Dorsey & Whitney LLP

(57) ABSTRACT

A method of magnetic resonance is provided that uses a frequency swept excitation wherein the acquired signal is a time domain signal is provided. In one embodiment, the sweeping frequency excitation has a duration and is configured to sequentially excite isochromats having different resonant frequencies. Acquisition of the time domain signal is done during the duration of the sweeping frequency excitation. The time domain signal is based on evolution of the isochromats.

16 Claims, 9 Drawing Sheets

U.S. PATENT DOCUMENTS 6,740,518 B1 * 5/2004 Duong et al. ............ 435/287.2
2005/0016276 A1 * 1/2005 Guan et al. ................... 73/579

OTHER PUBLICATIONS

Joshi, J. P. et al., "Rapid-scan EPR with triangular scans and fourier deconvolution to recover the slow-scan spectrum", *Journal of Magnetic Resonance,* Academic Press, Orlando, FL., vol. 175, No. 1, Jul. 2005, pp. 44-51, XP004929524.

R.K. Gupta et al., "Rapid Scan Fourier Transform NMR Spectroscopy", *Journal of Magnetic Resonance,* vol. 13, 1974, pp. 275-290, XP009076756.

Sindorf, D.W. et al., "Wide-Line NMR Spectroscopy in Solids Using Variable Frequency Pulses", *Journal of Magnetic Resonance,* Academic Press, Orlando, FL, vol. 85, No. 3, Dec. 1, 1989, pp. 581-585, XP000102286 ISSN: 1090-7807.

Davies, G.R. et al., "Continuous-Wave Magnetic Resonance Imaging of Short T2 Materials", *Journal of Magnetic Resonance,* Academic Press, Orlando, FL, vol. 148, No. 2, Feb. 2001, pp. 289-297., XP004406677.

J.W. Stoner et al., "Direct-detected rapid-scan EPR at 250 MHz", *Journal of Magnetic Resonance,* vol. 170, 2004, pp. 127-135, XP002414028.

J.-Y. Park et al., "Imaging Pseudo-Echoes Produced by a Frequency-Swept Pulse", *Proc. Intl. Soc. Mag. Reson. Med. 11,* 2004, p. 534, XP002414030.

Gatehouse, P.D. et al., "Magnetic Resonance Imaging of Short T2 Components in Tissue", *Clinical Radiology,* Livingstone, Harlow, GB, vol. 58, No. 1, Jan. 2003, pp. 1-19, XP009033520, ISSN: 0009-9260.

Madio, D.P. et al., "Ultra-Fast Imaging Using Low Flip Angles and Fids", *Magnetic Resonance In Medicine,* Academic Press, Duluth, MN, vol. 34, No. 4, Oct. 1, 1995, pp. 525-529, XP000535685, ISSN: 0740-3194.

A.H. Herlihy et al., "Continuous Scanning using Single Fast Spin Echo on a Short Bore Neonatal Scanner", *Proc. Intl. Soc. Mag. Reson. Med. 6,* 1998, p. 1942, XP002414435.

\* cited by examiner

FREQUENCY SWEPT EXCITATION FOR MAGNETIC RESONANCE

CROSS-REFERENCE TO RELATED APPLICATION(S)

This application claims benefit under 35 U.S.C. § 119(e) to U.S. Provisional Patent Application Ser. No. 60/725,361, filed Oct. 11, 2005, entitled "Frequency Swept Excitation for Magnetic Resonance Imaging", the content of which is incorporated herein in their entirety for all purposes.

GOVERNMENT FUNDING

This invention was made with Government support under Grant No.RR008079 awarded by the National Institutes of Health. The government has certain rights in this invention.

FIELD

A method of magnetic resonance is provided. More specifically, a method of magnetic resonance that uses a frequency swept excitation wherein the acquired signal is a time domain signal is provided.

BACKGROUND

Magnetic resonance techniques are applied in nuclear magnetic resonance (NMR) experiments and magnetic resonance imaging (MRI). In magnetic resonance techniques, the response of nuclear spins in a magnetic field is observed following excitation by a radio frequency (RF) field. There are three basic types of the RF excitation: sequential, simultaneous and random. Currently available techniques for both NMR and MRI using these types of RF excitation have limitations.

Several different NMR techniques have been developed including: continuous wave (CW), pulsed, stochastic, and rapid scan correlation spectroscopy.

Using CW techniques, an RF sweep is run exciting different resonating frequencies as a function of time. Typically the sweep has a low RF amplitude requirement. The CW sweep is run very slowly to maintain a steady state and avoid saturation of the signal. Thus, a large RF pulse will saturate the system and cannot be used. If the continuous wave sweep is run at a faster speed, "wiggles" will appear in the acquired signal. The resulting signal (or acquired signal) is looked at as a function of frequency. Historically, the first high resolution spectra of liquid samples were acquired using the CW technique. NMR spectroscopy using the CW technique became an important tool in the field of chemistry until the early 1970's. However, due to the slow rate of acquisition, CW NMR is time consuming and thus impractical for in vivo or clinical applications.

Pulsed Fourier Transform (FT) spectroscopy achieves efficiency and sensitivity beyond that of the CW technique. Using pulsed Fourier spectroscopy, a short, intense pulse at a constant frequency is applied that excites a plurality of resonances simultaneously. Typically, the pulse is a high power monochromatic RF pulse and there is a limited range of excitation frequencies. The resulting signal (or acquired signal) is looked at as a function of time. In the pulsed FT technique, the excitation pulse is generally assumed to be short (a delta function), so that the FT of this input function can be considered approximately equal to unity, and thus, the system spectrum ($H(\omega)$) can be obtained directly via FT of the impulse response ($h(t)$). FT spectroscopy can achieve high sensitivity because, during a given sampling time, a pulse may be repeated multiple times and the noise averaged. FT spectroscopy further has good flexibility insofar as the spin dynamic may be managed using a variety of different pulses.

Stochastic NMR uses a long series of small flip angle RF pulses whose phase or amplitude is modulated in a random manner. The spin system generally remains in the linear region. The technique typically involves several hundred pulses with a psuedo randomly determined phase. Phase is generally determined by Maximal Length Binary Sequence (MLBS). MLBS approximates white noise. Stochastic NMR has a broader range of excitation frequencies than does conventional FT pulsed NMR. Systematic noise inherent in images obtained with random noise excitation is eliminated by using pseudorandom noise together with Hadamard transformation for data evaluation. A back projection algorithm is used to reconstruct the images. A limitation in stochastic NMR is the need to create truly random excitation in order to avoid systematic noise artifacts. During excitation, a flip angle is used to define the angle of excitation for a field echo pulse sequence. The flip angle is the angle to which the net magnetization is rotated or tipped relative to the main magnetic field direction via the application of an RF excitation pulse at the Larmor frequency. The small flip angle used in stochastic NMR contributes to low sensitivity of the system. The acquired signal typically has a low amplitude. Further, hardware limitations frequently limit the utility of the system.

Rapid scan correlation spectroscopy combines the rapidity of FT NMR with the dynamic range of CW NMR. Rapid scan correlation spectroscopy uses a series of chirp pulses. The chirp pulses and the acquired pulses are correlated to produce a spectra. While rapid scan correlation spectroscopy is faster than CW NMR, its slow speed remains a limitation in its application.

In the evolution of high resolution NMR, pulsed Fourier NMR spectroscopy has continued to dominate the field, while the CW NMR technique essentially became obsolete and was used only for niche applications.

The above discussion relates specifically to high resolution NMR, typically performed in a laboratory setting on sample objects generally of test tube size. Another field of application for magnetic resonance techniques is clinical applications, in vivo applications, or MRI applications. MRI has technical requirements beyond those of NMR. Because the objects of interest (such as the brain or breast) is usually much larger than a test tube, the static and RF fields used in MRI are more inhomogeneous than those used in high resolution NMR. For applications on living systems, the need to avoid tissue heating places limits on the intensity and duty cycle of the RF irradiation that can be safely used, also known as the specific absorption rate (SAR) limitations. Similarly, when used in vivo, the subject must remain generally stationary during the MRI. Thus, slow techniques are difficult in clinical applications.

Several MRI techniques have been developed including CW MRI, pulsed FT MRI, including, Ultra-short Echo Time (UTE) MRI, and stochastic MRI. Additionally, rapid scan techniques have been considered for imaging using electron paramagnetic resonance (EPR).

Continuous wave MRI system using low RF power has been applied to study a variety of heterogeneous materials exhibiting very short relaxation values. As with CW NMR, CW MRI must be run at a very slow rate. This rate typically precludes application in clinical applications.

Pulsed FT MRI is useful in imaging of soft tissue but has limitations in the imaging of materials having fast relaxing spins (including semi-solid objects such as bone). These techniques use a short monochromatic RF pulse for excitation, followed immediately by signal acquisition, all performed in the presence of a field gradient. In MRI applications, the RF pulse can approach a delta function only by restricting the flip angle to <<90°. As the pulse length increases, the pulsed FT spectrum suffers from increasing phase and baseline distortions. Further, although these fast imaging sequences have minimal demands on gradient hardware performance, they are severely limited by the length of the pulse. To achieve broadband excitation with limited $\omega_1$ amplitude, a small flip angle is employed, which results in low S/N. Specifically, the width of the pulse leads to low sensitivity and low contrast in clinical applications. Artifacts such as increasing phase and baseline distortions can be avoided by replacing the free induction decay (FID) with an echo acquisition. Echo time is the time between the application of a pulse and the peak of the echo signal in spin-echo pulse sequences. However, the finite echo time used to form an echo leads to reduced sensitivity to fast relaxing spins and increased susceptibility to motion and flow artifacts. For imaging of objects having fast relaxing spins, the echo time must be short.

One of the pulsed FT MRI methods—Ultrashort Echo Time (UTE) was developed to image fast relaxing spins using FID acquisition. The UTE sequence employs a self refocused excitation pulse, followed immediately by a pulsed-on gradient and signal acquisition. UTE MRI has short "echo" times, which is good for imaging of fast relaxing spins. However, UTE pulse sequences use a growing gradient and simultaneous acquisition. The gradient slew rate is the rate of ascent or descent of a gradient from zero to its maximum amplitude, either positive or negative. The shorter the rise time, the faster the gradients and smaller echo time. As a result, UTE has better sensitivity to fast relaxing spins. Thus, it is generally desirable that the gradient have a fast slope. Using UTE MRI, there is a gradient limitation that limits the resolution of the images. The minimum duration needed to execute the excitation pulse and gradient switching are limited by the available RF amplitude and the gradient slew rate, respectively.

As discussed with respect to stochastic NMR, stochastic MRI has a small flip angle and thus has low sensitivity and low contrast in imaging.

While not currently implemented in MRI, rapid scan techniques have been used in electron paramagnetic resonance (EPR). These techniques have generally been considered unsuitable for MRI because of the following difficulties. Rapid scan utilizes a fast gradient echo sequence such as a series of chirp pulses. To avoid non-uniform weighting of the spectrum, the excitation frequency must be swept linearly (chirp pulse), which excludes the use of tailored frequency sweeps. Generally, an excitation profile in MRI applications must be rectangular. This is not readily achievable using short chip pulses and, thus, a rapid scan MRI using such chirp pulses would result in a relatively bad excitation profile. In rapid-scan FT techniques, the detector frequency is synchronous with the time-dependent transmitter frequency, and thus, correlation must be used to restore the undistorted absorption line by removing the "ringing" that persists following passage through resonance. In accordance with the Nyquist theorem, sampling in the frequency versus time domain places an upper limit on the sweep rate. Thus, rapid scan FT MRI, even if suitable for implementation, has an inherent speed limitation and its slowness limits use in clinical applications.

Using available techniques, it is difficult to image objects having a broad distribution of relaxation times, including very short spin-spin relaxation times, such as semi-solid objects including bone, macromolecules, and quadripolar nuclei. Accordingly, it would be desirable to have a technique to image materials having short spin-spin relaxation times that is sufficiently fast for in vivo application.

SUMMARY

A method of magnetic resonance is provided that uses a frequency swept excitation wherein the acquired signal is a time domain signal is provided.

In one embodiment, the method comprises, applying a sweeping frequency excitation and acquiring a time domain signal. The sweeping frequency excitation has a duration and is configured to sequentially excite isochromats having different resonant frequencies. Acquisition of the time domain signal is done during the duration of the sweeping frequency excitation. The time domain signal is based on evolution of the isochromats.

In another embodiment, the method comprises exciting a specimen with a sweeping frequency excitation, acquiring a time domain signal from the specimen, and processing the acquired time domain signal. The frequency excitation has a plurality of alternating excitation segments and quiescent segments. The excitation segments are modulated according to at least one of a phase modulation function and a frequency modulation function. The acquired time domain signal is based on resonance during a plurality of the quiescent segments.

While multiple embodiments are disclosed, still other embodiments of the present invention will become apparent to those skilled in the art from the following detailed description. As will be apparent, the method disclosed herein is capable of modifications in various obvious aspects, all without departing from the spirit and scope of the present techniques. Accordingly, the detailed description is to be regarded as illustrative in nature and not restrictive.

DETAILED DESCRIPTION

Figure 1:
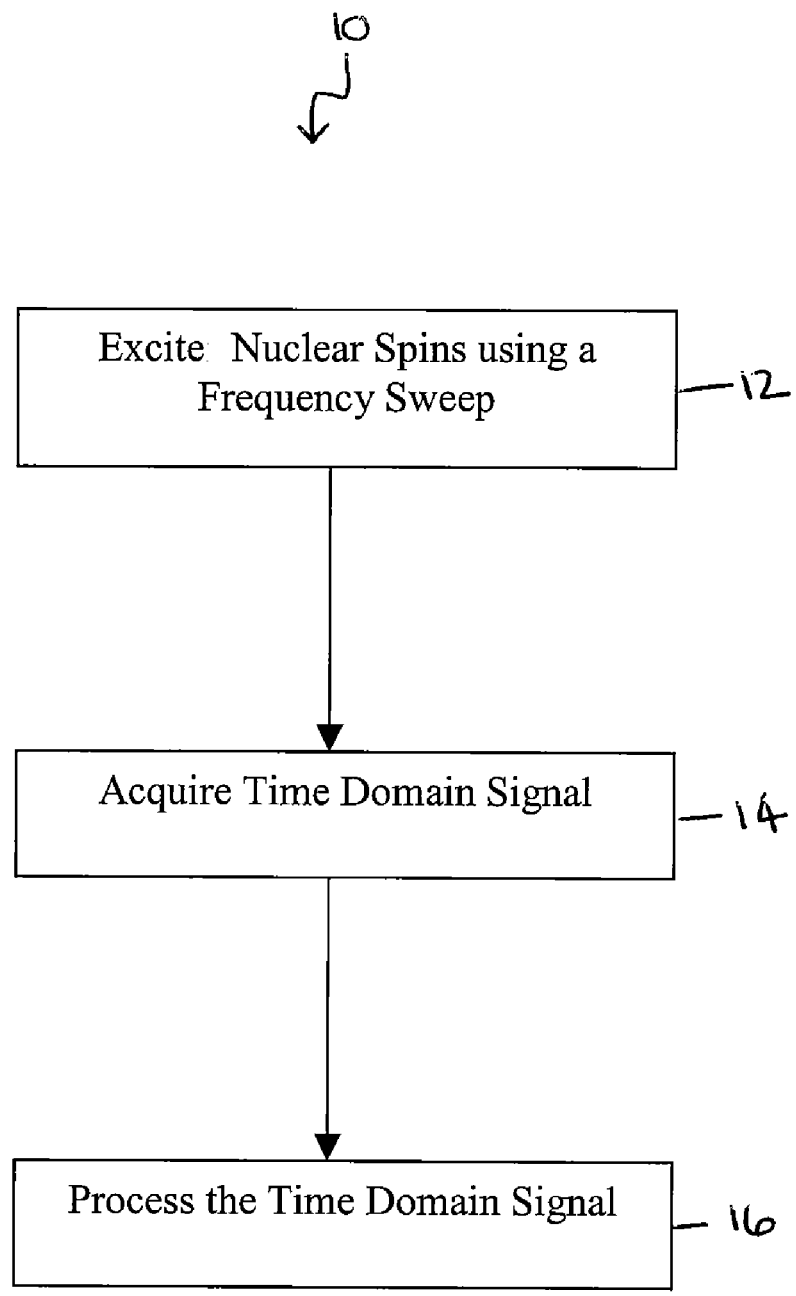
FIG. 1 illustrates a frequency swept excitation method in accordance with one embodiment

A method of magnetic resonance is provided that uses a frequency swept excitation wherein the acquired signal is a time domain signal. The method may be referred to as a frequency swept excitation method and has applications in a plurality of fields including, but not limited to, human and animal medicine, dentistry, material science, security, and industry. The frequency swept excitation method may be used in nuclear magnetic resonance spectroscopy, magnetic resonance imaging, electron paramagnetic resonance (EPR), nuclear quadrupole resonance (NQR), and others. The frequency swept excitation method may be used in studies of fast relaxing spins as well as magnetic resonance imaging using non-uniform (inhomogeneous) magnets or in imaging of inhomogeneous fields.

Using the frequency swept excitation method, excitation of nuclear spins is achieved using a radio frequency sweep. In one embodiment, the excitation comprises a series of pulses, each pulse having an excitation segment and a quiescent segment. The frequency or phase is swept within each pulse. A signal is acquired as a time domain signal during the quiescent segment. Acquiring the signal during the quiescent segment, and thus during a portion of the excitation pulse, may be referred to as acquiring in a time-shared manner. The acquired signal is treated as a signal that varies as a function of time and is looked at in the time domain. After signal acquisition, the signal is processed, for example using a correlation method or a convolution, to correct the acquired signal by separating the spin system spectrum. The processed signal can then be used in imaging. Generally, the method affords fast and quiet magnetic resonance imaging. Standard MRI scanners may be programmed to use the frequency swept excitation technique.

In one embodiment, the frequency swept excitation method uses time shared acquisition by incorporating an excitation segment and a quiescent segment during the RF sweep such that excitation and acquisition are nearly simultaneous. In another embodiment, the frequency swept excitation method performs excitation and acquisition simultaneously, for example by decoupling the receiver and transmitter. Either of the time-shared or simultaneous embodiments of the frequency swept excitation method may be used for imaging objects having a broad distribution of relaxation times, including very short spin-spin (or transverse or $T_2$) relaxation times. In some embodiments, the frequency swept method is sensitive to all excited spins having spin-spin relaxation time larger than the reciprocal value of the spectral width (thus, $T_2 > 2\pi/sw$). Using conventional MRI techniques, excitation and acquisition events are separated by the length of time known as the echo time ($T_E$), which is typically >1 ms. This length of time is generally too long to allow detection of slowly tumbling nuclei with short spin-spin relaxation time ($T_2$). Accordingly, using conventional MRI techniques, it is difficult to image objects having short spin-spin relaxation times.

The present method has a near zero echo time (or $T_E$ approaching 0) because signal acquisition can begin within a few microseconds after excitation. Alternatively, the method may have a zero echo time where signal acquisition occurs during excitation. Because the frequency swept method has a zero or near zero "echo time," it is generally less sensitive to motion and flow artifacts than conventional magnetic resonance methods. Thus, the frequency swept method has a reduced signal loss due to either diffusion in the presence of a gradient or uncompensated motion as compared with other magnetic resonance methods. The frequency swept excitation method may be beneficial for studying objects having very fast spin-spin relaxation rates such as macromolecules, semi-solids, and quadripolar nuclei. Examples of quadripolar nuclei that may be imaged include sodium-23 MRI, potassium-39, and boron-11. The present method is further insensitive to field inhomogeneity and thus can be used, for example, in imaging tissues near metal objects such as metal implants. Further, the method may be used in magnetic resonance imaging and spectroscopy using non-uniform (inhomogeneous) magnets (for example, having inhomogeneous main magnetic field or RF field).

In various embodiments, frequency swept pulses improve signal-to-noise (SNR) ratios, suppress artifacts, improve experimental accuracy, and reduce peak RF power. The frequency swept method generally is relatively quick because it avoids delays associated with refocusing pulses or gradient inversion and combines the time used for excitation with the time used for acquisition. Because different frequencies may be excited sequentially the resulting signal is distributed in time, leading to a decreased amplitude of the acquired signal. This allows more effective utilization of the dynamic range of a digitizer. Further, because the frequency swept method may use a small step when changing gradients between projections, the fast gradient switching of conventional magnetic resonance techniques that creates loud noise can be avoided. This property can be important for MRI scanning of the patients having ligyrophobia.

As shown in FIG. 1, in accordance with one embodiment, the frequency swept excitation method 10 excites 12 nuclear spins using a frequency sweep. In one embodiment, the sweep comprises a series of pulses, each pulse having excitation segments and quiescent segments. After excitation, an acquisition signal is acquired 14 from which an image may ultimately be produced. The acquisition signal is acquired as a time domain signal. In one embodiment, signal acquisition is done during the quiescent segments of each pulse. After signal acquisition, the signal is processed 16 to extract the useful signal from the acquired signal (system response). Processing (also referred to as post processing) may be done, for example, by correlation or convolution. Using the frequency swept method, the spin response to the swept RF excitation behaves effectively as a linear system for flip angles up to 90°. Hence, the frequency swept method affords high S/N without observable image artifacts from violating the linearity condition.

To use the frequency swept method for NMR measurements, the signal is recorded, and to perform MRI, a procedure is implemented to encode spatial information. Ways to accomplish this are described herein. As described, each pulse of a series of pulses is divided into a plurality of segments (e.g., 512) separated by short delays (e.g., 10 μs each), and during each of these short delays, an analog-to-digital converter (ADC) samples one or more points. These short delays used for signal recording have no or minimal effect on pulse performance or the steady state.

Excitation

As shown in FIG. 1, nuclear spins in the object of interest are excited 12 using a frequency sweep. The frequency sweep may comprise a series of frequency modulated pulses, also referred to as a series of frequency-swept pulses. In one embodiment, the frequency excitation is non-random but may not be continuous or linear. The pulses may be generated in any suitable manner, for example using a transmitter as is known in the art. The frequency-swept pulses sequentially excite isochromats over each pulse, and as a result, the phase of the magnetization varies in a quadratic manner along the readout direction. In accordance with one embodiment, the frequency of the RF irradiation used to excite signals is modulated in time during each pulse. In accordance with another embodiment, the phase of the RF irradiation used to excite signals is modulated in time during each pulse. Thus, the signals are continually out of phase. The frequency-swept excitation distributes the signal energy in time. Dynamic range requirements for proper signal digitization and peak RF power requirements are thereby reduced compared with conventional MRI.

While discussion is made of sweeping the frequency during each pulse, such sweeping may alternatively be done by sweeping the phase during each pulse. Thus, the pulses may alternatively be referred to as phase-swept or phase modulated.

Figure 2:
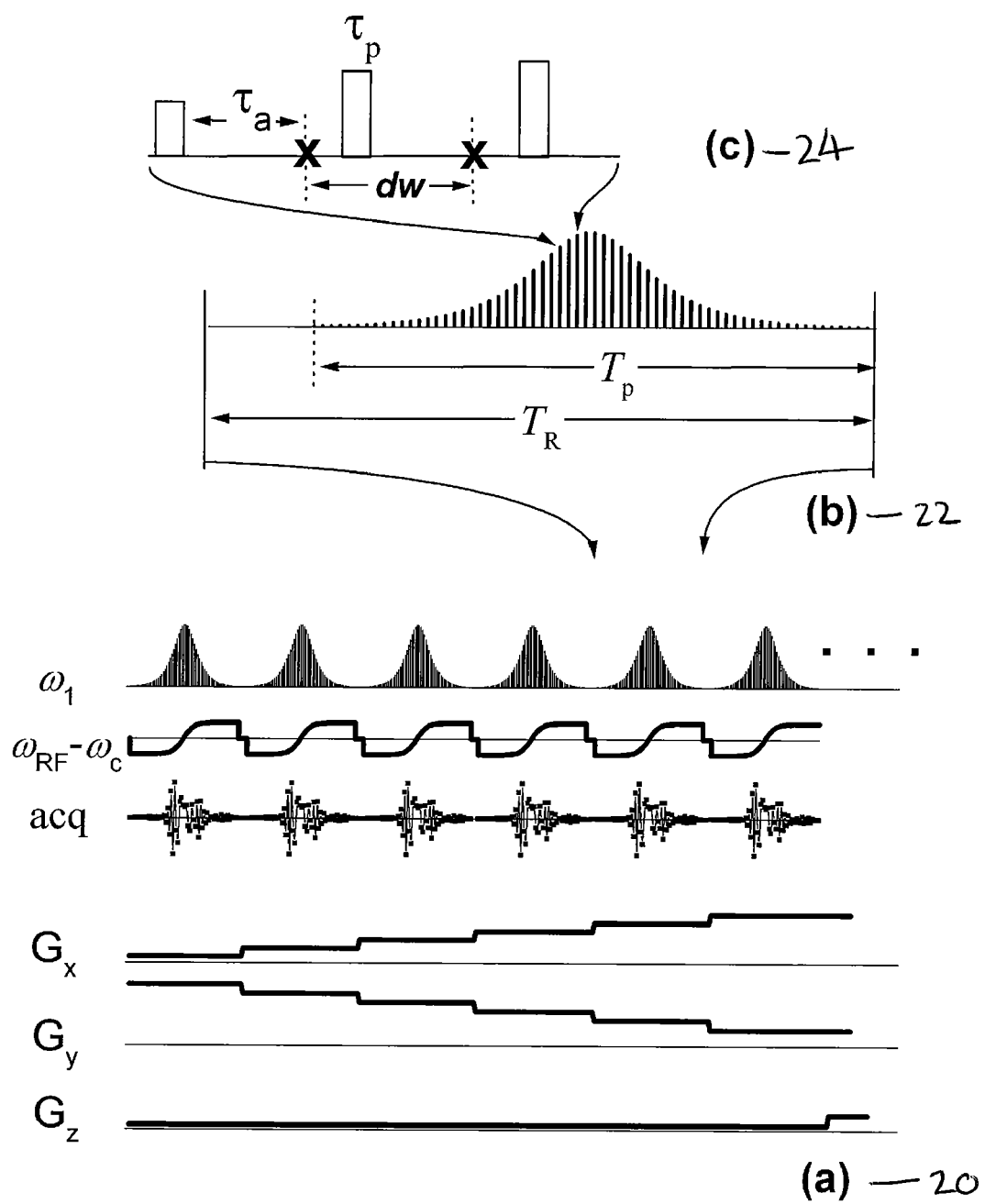
FIG. 2 illustrates a pulse sequence scheme in accordance with one embodiment.

An example pulse sequence scheme 20 is illustrated in FIG. 2. In the embodiment of FIG. 2, the pulse sequence comprises a series of pulses, each pulse comprising excitation segments and quiescent segments. In alternative embodiments, the transmitter and receiver may be decoupled and quiescent segments may not be used. In one embodiment, the pulse sequence is delivered while a gradient is applied, as discussed with respect to signal acquisition. The gradient magnetic field can be used to alter (collectively and sequentially) the influence of the static magnetic field B0 on the imaged object by increasing or decreasing the field strength.

FIG. 2 illustrates pulse sequence scheme 20, a presentation of the repeated part of the sequence 22, and a magnified view of the pulse segments 24. The scheme 20 employs a sequence of RF pulses (for example, p pulses wherein p represents the number of pulses), each having a duration $T_p$. In one embodiment, $T_p$ is in the millisecond range. Each pulse is divided into N segments, each having RF power on for duration $\tau_p$ following a delay with RF power off. Thus, each pulse comprises an excitation segment and a quiescent segment. Thus, as shown in the repeated part of the sequence 22, the scheme employs p frequency-modulated pulses with a repetition time $T_r$ that exceeds the pulse length $T_p$. In one embodiment, the repetition time $T_r$, exceeds the pulse length $T_p$ by at least the amount of time needed for setting a new value (or orientation) of a magnetic field gradient used to encode spatial information for signal acquisition. The images may be processed using a 3D back-projection reconstruction or using regridding with followed FT, although other acquisition and reconstruction methods are possible.

The RF pulses may be of the family of hyperbolic secant (HSn) pulses which utilizes both amplitude and frequency modulation. As will be discussed more fully below, in some embodiments, the RF pulses are run at a linear or subadiabatic range. A transition may be made from the adiabatic to the linear region by reducing the RF amplitude or increasing the sweep rate, while other pulse parameters remain constant. The amplitude ($\omega_1(t)$) of the pulse may be written as:

$$\omega_1(t) = \gamma B_1(t), \quad (1)$$

(in units of rad/s) where $\gamma$ is the gyromagnetic ratio and $B_1(t)$ is the time-dependent amplitude of the RF field. The time dependency of amplitude ($\omega_1(t)$) and phase ($\omega_{RF}(t)$) of HSn pulses can thus be written as, $$\omega_1(t) = \omega_{1\max} \mathrm{sech}(\beta(2t/T_p - 1)^n) \quad (2)$$

$$\omega_{RF}(t) = \omega_c + \frac{B_\omega C}{2} \int_0^t \mathrm{sech}^2(\beta(2\tau/T_p - 1)^n) d\tau \quad (3)$$

where $\omega_{1max}$ is the maximum pulse amplitude, $\omega_c$ is the carrier frequency (usually the center frequency in the sweep range), $B_\omega$ is the total bandwidth of the frequency sweep, $T_p$ is pulse length, $\beta$ is a dimensionless truncation factor (sech ($\beta$)=0.01), and C is a normalization factor given by $$C = \left[ \int_0^t \mathrm{sech}^2(\beta\tau^n) d\tau \right]^{-1}. \quad (4)$$

As shown at 20 of FIG. 2, the frequency swept pulse is represented as a histogram of N different pulse elements with amplitudes $\omega_1(t)$ and offset frequencies $\omega_{RF}(t)-\omega_c$. The excitation bandwidth is not constrained by the amplitude of $\omega_1$. Delays $\tau_a$ are inserted into the pulse pattern after each pulse element of duration $\tau_p$, making a dwell time $dw=\tau_p+\tau_a$. The receiver is blanked during $\tau_p$ and open during $\tau_a$ for data sampling. Data sampling, discussed below, is performed during $\tau_a$, shown in the magnified view of the pulse segments 24. The introduction of delays into the pulse shape leads to a basically unmodified excitation profile.

The relationship between the continuous HSn pulse and its time-shared variant (shown) is analogous to the relationship between a long pulse of constant amplitude and a DANTE pulse train which closely approximates the excitation profile of the continuous pulse, but produces excitation sidebands at multiples of the pulse repetition rate. Because the repetition rate of the pulse elements and the acquisition rate may be equal to the inverse dwell time, the first excitation sideband is generally set outside of the acquisition spectral window. The offset frequencies may be created by incrementing the phases of pulse elements. In this case the maximum reachable excitation bandwidth according to the Nyquist theorem is approximately equal to the acquisition spectral width (s$\omega$):

$$B_\omega^{\max} = 2\pi \frac{N}{T_p} = s\omega \quad (5)$$

when the maximum phase increments (in this case, at the beginning and end of the pulse) are equal to $\pi$. By proportionally decreasing the phase increments, only a portion of spectral window may be excited.

Figure 3:
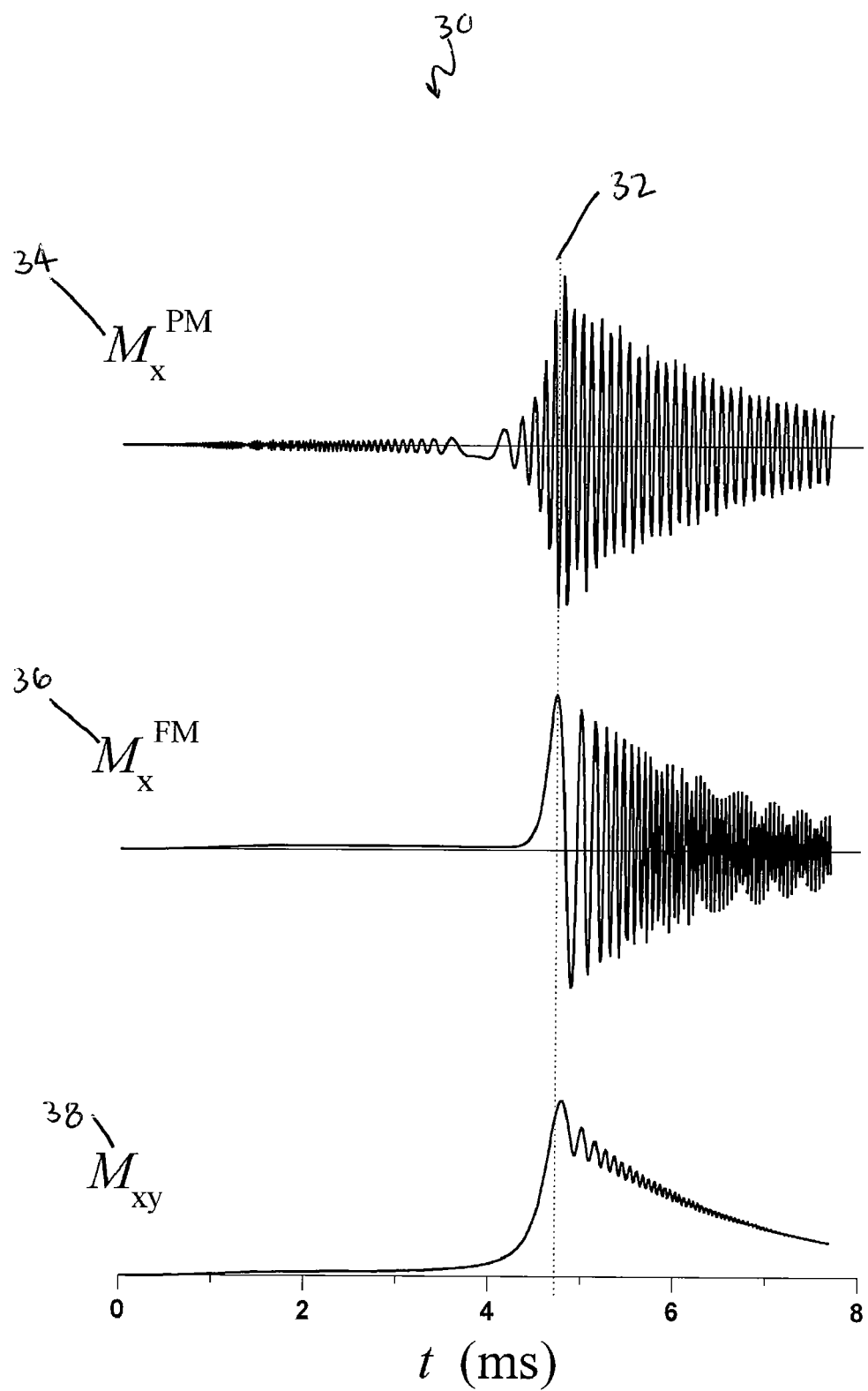
FIG. 3 illustrates simulation results in the phase-modulated and frequency-modulated rotating frames, and the magnitude, of a single isochromat, using a frequency-swept excitation in accordance with one embodiment.

One can assume that the RF field excites each isochromat instantaneously when its resonance frequency is attained in the frequency sweep. FIG. 3 illustrates the oscillatory motion 30 of the magnetization components of a given isochromat having frequency $\omega$. The isochromat excitation time in FIG. 3 is shown by the vertical dotted line 32. In FIG. 3, $M_x^{PM}(t)$ 34 presents the x-axis component of the transverse magnetization vector of the isochromat in a reference frame known as the phase-modulated (PM) frame, which rotates around the static magnetic field direction (z) with an angular velocity $\omega_c$ equal to the center frequency in the sweep range. $M_x^{FM}(t)$ 36 is the x-axis component in a frequency-modulated (FM) frame, which rotates synchronously with the (time-dependent) pulse frequency $\omega_{RF}(t)$. FIG. 3 also shows the absolute value of the transverse magnetiziation $M_{xy}(t)$ ($\sqrt{M_x^2(t)+M_y^2(t)}$) 38. Similar oscillatory behavior may arise in the rapid passage, linear region, which satisfies the conditions $$aT_2^2 >> 1 \quad (6a)$$

and $$a/\omega_1^2 >> 1, \quad (6b)$$

where $\alpha$ is the sweep rate; in this example $\alpha \approx B_w/2\pi T_p$. As may be appreciated, a difference arises between the rapid passage, linear region and the rapid passage, adiabatic region, wherein the latter condition is $\alpha/\omega_1^2 \ll 1$. Accordingly, the transition from the adiabatic to the linear region requires reducing the RF amplitude or increasing the sweep rate, while other pulse parameters remain constant. In this way, an adiabatic passage pulse, such as a HSn pulse, can be used in the rapid passage, linear region to rotate the magnetization by an angle <90°. Below, all presented simulated and experimental data were generated using excitation in the rapid passage, linear region.

The frequency swept excitation method sequence has less stringent constraints than indicated by Eqs. (6a) and (6b). First, because the pulse is segmented, the average value of $\omega_1(t)$ scales inversely with $\tau_p/dw$. Second, the correlation method, described below, works well up to a rotation angle near 90° before significantly violating the linearity condition of Eq. (6b). The frequency swept excitation method is not restricted to the rapid passage region by Eq. (6a). For example, the frequency swept excitation method may also be used in the intermediate passage, linear region, with the consequences of sacrificing signal-to-noise ratio (S/N) and resolution.

FIG. 3 illustrates that the isochromat begins its motion slightly before resonance is reached and thereafter decays. The wiggles before the excitation time observed in PM frame fully disappear in FM frame. Thus, the wiggles are not a function of the resonance frequencies of the isochromats and instead depend only on the frequency-modulated function $\omega_{RF}(t)$. In other words, until the moment resonance is attained, the isochromat follows the effective RF field vector to the transverse plane. At the time of resonance, the isochromat is released from the RF pulse's influence and has an almost free precession with a small decaying modulation which can be seen in magnitude mode (see 24 of FIG. 2) as wiggles after the resonance time. Because these wiggles have a variable frequency, after Fourier transformation (during processing, described below) their contribution is spread across the resulting spectrum. The spectral contamination arising from wiggles of different isochromats are additive and thus are more prominent when imaging is performed on an ensemble of isochromats.

Acquisition

As shown in FIG. 1, a time domain signal is acquired 14. Signal acquisition can be done nearly simultaneously with excitation. Specifically, signal acquisition may be done during quiescent segments of a pulse. In accordance with the Nyquist theorem, sampling in the frequency versus time domain places a lower limit on the sweep rate used the frequency swept method but places no upper limit on the sweep rate. The lack of an upper limit on the sweep rate is especially advantageous for MRI applications. In alternative embodiments, signal acquisition may be simultaneous with excitation.

Signal acquisition may be done in any suitable manner, for example using a receiver to measure current, voltage, impedance, or other, as is know in the art. In one embodiment, the receiver is set to a constant frequency and thus the acquired signal behaves as $M_x^{PM}$, shown in FIG. 2, with the abscissa representing time (t). Following the excitation time (dotted line), the ensuing evolution resembles a FID. To obtain the spectrum, correlation, described below, may be used to remove the influence of the $\omega_{RF}(t)$ function and to unscramble the phases of different isochromats having different excitation times.

As previously discussed and shown in FIG. 2, the frequency swept pulse is represented as a histogram of N different pulse elements with amplitudes $\omega_1(t)$ and offset frequencies $\omega_{RF}(t)-\omega_c$. In one embodiment, delays $\tau_d$ are inserted into the pulse pattern after each pulse element of duration $\tau_p$, making a dwell time $dw=\tau_p+\tau_d$. The receiver is blanked during $\tau_p$ and open during $\tau_d$ for data sampling. Thus, in one embodiment, acquisition (or data sampling) is performed during the delay $\tau_d$ (also referred to as a quiescent segment), after the pulse segment. More specifically, referring to FIG. 2, data sampling is performed at time $\tau_a$, shown in part c of Figure, using a time-shared method. Because excitation is temporarily suspended during the delay, acquisition may be performed without acquiring the RF pulse. Thus, the frequency sweep is broken into excitation segments and quiescent segments wherein acquisition is performed during the quiescent segments and, thus, during the frequency sweep. This is referred to as time-shared excitation and signal acquisition. In some embodiments, signal acquisition may start before the quiescent segment or extend beyond the quiescent segment. In alternative embodiments, acquisition may be performed simultaneously with excitation by decoupling the transmitter and transceiver, thereby avoiding acquisition f the RF pulse.

The time-shared excitation and signal acquisition maybe done in the presence of an applied magnetic field gradient. Magnetic field gradients are used to change the strength of the magnetic field $B_0$ in a certain direction. The magnetic field gradient can be used to select a region for imaging and also to encode the location of MR signals received from an object being imaged. In one embodiment, the applied magnetic field gradient is: $G=(G_x \hat{i}+G_y \hat{j}+G_z \hat{k})$. The field gradient is used to impart on the spins a spatially dependent Larmor frequency $\omega(r)=\gamma(Gr+B_0)$, where r is the coordinate vector and $B_0$ is the static magnetic field. In one embodiment, the field gradient used for spatial-encoding is stepped in orientation in an incremental manner, which results in low acoustic noise—as opposed to techniques wherein the field gradient is pulsed on and off.

In one embodiment, the minimum temporal spacing of pulses, or repetition time $(T_R)$, is $T_p$ plus the amount of time $(t_G)$ needed to make an incremental change in the orientation of G. After acquiring frequency-encoded projections, 3D images can be reconstructed, for example by using a 3D backprojection algorithm or gridding. In one embodiment, the minimum acquisition time required to obtain each projection is $$A_t = t_G + 2\pi N/sw. \quad (7)$$

For example, with acquisition parameters that standard MRI scanners can readily achieve, $sw/2\pi=100$ kHz and $t_G=0.3$ ms, a 3D image with matrix size=128×128×128 can be acquired in less than 30 s. A further ~30% time reduction is possible without affecting image quality using an equidistant projection sampling method.

In one embodiment, acquisition is done radially. Every spectrum that is taken by applying a gradient gives one projection of the object: a projection of the object to gradient direction. To reconstruct an image of the object, the object is viewed from different angles. Thus, to create an image, it may be desirable to sample points along a predefined set of angles in a hemisphere or sphere. Generally, each point viewed may be equidistant from another point such that the sampling is isotropic. The more projections used, the more resolved resulting image is after reconstruction. That said, looking at an object from one direction (for example the Y direction) will give the same projection as looking at the image from the opposite direction (for example the −Y direction) with the projection being changed from left to right or right to left. Thus, a half circle (for a 2d image, angle=0-180) or a hemisphere (for a 3d image) can be used to construct an image; the other half circle or hemisphere will provide the same projection in the opposite direction. However, in some circumstances it may be desirable to take projections from each direction because taking images from each direction (for example, Y and 'Y) can give information about artifacts. However, while there may be some advantages to sampling the entire sphere (for example, to minimize artifacts through cancellation), sampling the entire sphere takes twice as much time as sampling a hemisphere. Thus, sampling a hemisphere and minimizing artifacts through processing and post processing may be done. In one embodiment, sampling is done radially along the hemisphere such that the view ordering is generally 2 or 3d radial ordering.

In taking projections, the object is imaged from different angles. For ease of explanation, a 2D image is referred to, however it is to be understood that this discussion applies equally to a 3D image. If an object is viewed along a half circle, the image is viewed from an angle of 0 to an angle of 180. In viewing the object, projections are taken at a plurality of angles from 0 to 180, inclusive. Thus, for example, the object may be viewed N times (for example, 181 times, starting at an angle of 0 and ending at an angle of 180), stepping the angle of the projection in 1 degree increments. When sampling is done in order along a stepped sequence, it may be referred to as sequential sampling. The order of taking the views is referred to as view ordering.

Post Processing

To extract useful information from the spin system response, post processing is done to correct the acquired signal. Thus, as shown in FIG. 1, the time domain signal may be processed 16. Post processing may be done, for example, using a correlation method or a convolution method. As will be described, correlation 40 comprises Fourier transforming the excitation signal and the acquired time domain signal and processing the FT signals in the frequency domain, shown in FIG. 4a. Deconvolution 50 comprises processing the excitation signal and the acquired time domain signal in the time domain and Fourier transforming the processed signals, shown in FIG. 4b. In some embodiments, the frequency swept excitation method may be operated in a rapid updated mode to reach high temporal resolution in dynamic studies. This pseudo-temporal resolution is possible because projection reconstruction, unlike phase encoded imaging, samples the center of k-space with every acquisition. This acquisition method is relatively insensitive to sample motion, which is advantageous for imaging live objects.

To obtain an image of an object using the frequency swept method, additional steps may be performed to remove the $\omega_{RF}(t)$ oscillations described above, since simple Fourier transformation of the time-domain signals may yield a spectrum (in this case, a projection of the object) that is contaminated by the frequency components of $\omega_{RF}(t)$. In one embodiment, processing maybe done using a correlation method. Accordingly, the spin system response is treated as a linear system. As may be appreciated by one skilled in the art, adiabatic pulses are typically run in an adiabatic region. The adiabatic region is a non-linear region. In order to correlate the acquired signal as a linear system, it may be useful to perform excitation in a linear region such as a sub-adiabatic region. In some embodiments, excitation may be performed in a linear region.

Figure 4A:
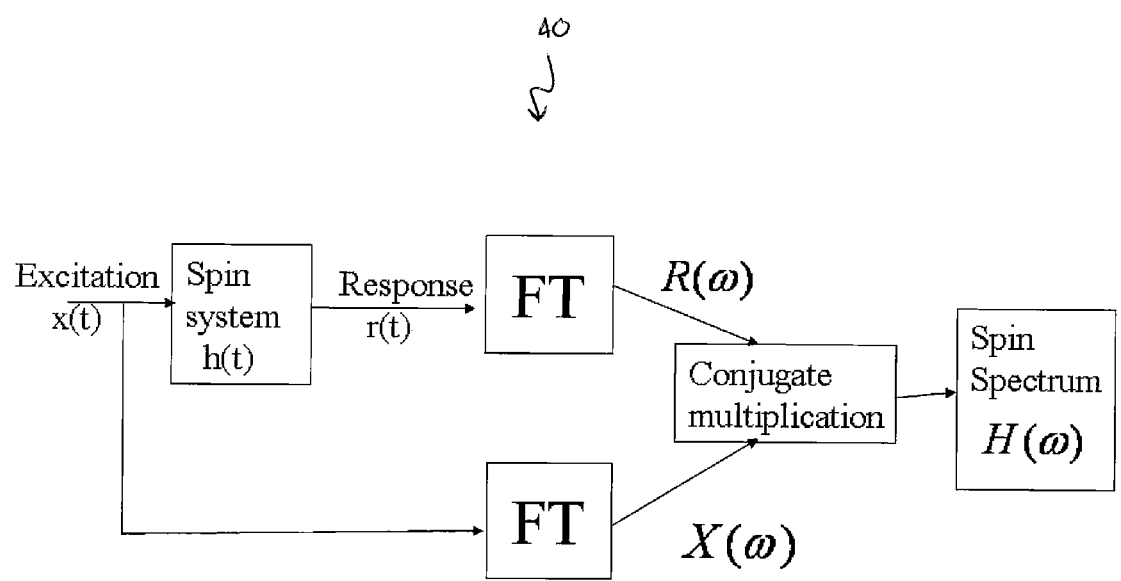
FIG. 4A illustrates correlation processing in accordance with one embodiment.
Figure 4B:
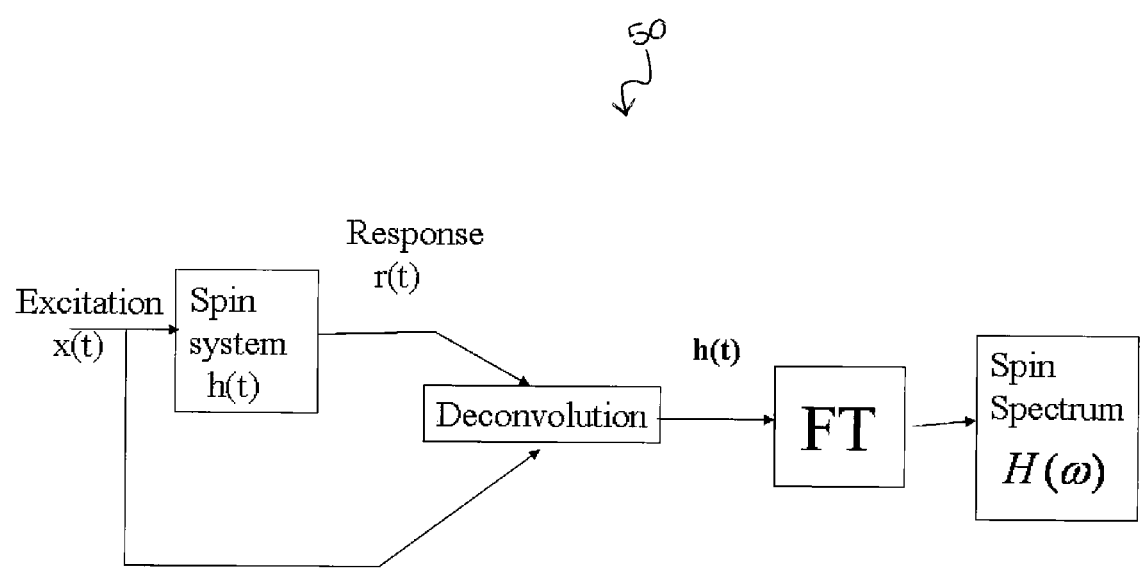
FIG. 4B illustrates convolution processing in accordance with one embodiment.

The response r(t) of the linear system to the input function x(t) is the convolution process 50, shown in FIG. 4b, given by $$r(t)=h(t) \otimes x(t). \qquad (8)$$

The linear system to which an input x(t) may be applied and from which a response r(t) comes. According to the standard nomenclature used in NMR, the unit impulse response h(t) is represented as the free induction decay (FID) and the unit frequency response function is the spectrum H(ω). These functions are related to one another by direct Fourier transformation. According to Fourier theory, the convolution in the time domain is a complex multiplication in the frequency co-domain:

$$F\{r(t)\}=R(\omega)=H(\omega)X(\omega), \qquad (9)$$

where X(ω) is a Fourier transformation of the input function x(t), which is the complex pulse function x(t) given by:

$$x(t)=\omega_1(t)\exp(-i(\omega_{RF}(t)-\omega_c)t) \qquad (10)$$

Alternatively, the spectrum of the system can be retrieved by using a correlation method 40, shown in FIG. 4a, which may be performed in the frequency domain with complex conjugate multiplication by the pulse function, as:

$$H(\omega) = \frac{R(\omega)X^*(\omega)}{|X(\omega)|^2}. \qquad (11)$$

where |X(ω)| is the modulus of X(ω). The spectral profile of the HSn pulses is generally uniform within the bandwidth, and as a result, |X(ω)| is generally constant across the spectrum.

Figure 5:
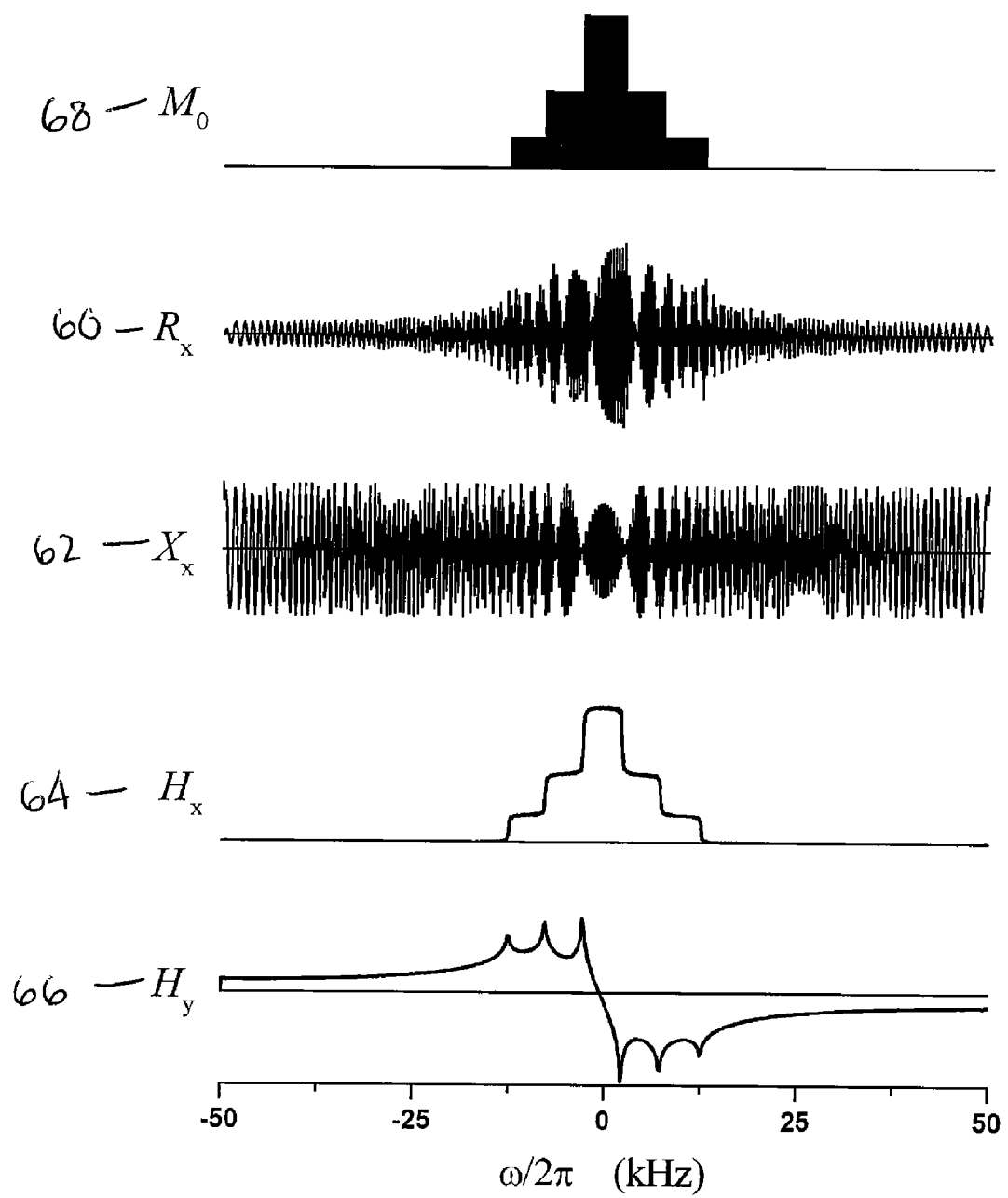
FIG. 5 illustrates real parts of a response and RF pulse spectrum and real and imaginary parts of a system spectrum in accordance with one embodiment.

FIG. 5 illustrates one embodiment of a correlation method. FIG. 5 shows real parts of the response ($R_x$) 60 and the RF pulse spectrum ($X_x$) 62, and the real ($H_x$) 64 and imaginary ($H_y$) 66 parts of the system spectrum. These are shown in the frequency domain wherein the excitation amplitudes are weighted according to a step function, $M_O(\omega)$ 68. $X_x$ 62 represents the Fourier transform of an RF pulse patter. $R_x(\omega)$ 60 has scrambled phase and contains contaminant signals arising from the $\omega_{RF}(t)$ oscillations, which contain all frequencies in the spectral window. From a qualitative comparison, good correlation between $X_x$ 62 and $R_x$ 60 is apparent. The excitation profile of the HSn pulses is uniform within the bandwidth as result of |x(ω)| being generally constant across the spectrum. The spectrum of the system shown by $H_x(\omega)$ 64 generally replicates the spin density profile $M_O(\omega)$ 68. The correlated absorption spectrum of the system $H_x$ 64 was obtained from Equation 11 and by applying a first order phase correction on angle α(ω), where $$\alpha(\omega) = \pi \frac{(\omega - \omega_c)}{\omega_c} \frac{\tau_p}{dw} \qquad (12)$$

As shown in FIG. 5, contamination from wiggles are observed only in the imaginary part of the signal. Consequently, the real part is the spectrum which is the same as that obtained after Fourier transformation of an ordinary free induction decay and thus can be used for the spectroscopy or image reconstruction. Thus, in some embodiments, only the real part of the phased projections is used. In some embodiments, the complex projections can be used, for example with deleting the pulse contamination during reconstruction. Thus, FIGS. 4a and 4b illustrate processing using correlation 40 and deconvolution 50 methods, respectively. In FIG. 4a, the excitation signal (x(t)) and the acquired time domain signal (h(t)) are Fourier transformed followed by conjugate multiplication to generate a signal (H(w)). In FIG. 4b, the excitation signal (x(t)) and the acquired time domain signal (h(t)) are decorrelated and the decorrelated signal (h(t)) is Fourier transformed to generate a resulting spectrum(H(w)). The processes illustrated in FIGS. 4A and 4B return the same signal (H(w)).

The processing discussed above is based on treatment of the acquired signal as time domain signal. However, the excitation sweep is a function of both time and frequency and thus may be treated in either of the time domain or the frequency domain. In some embodiments, two spectra may be generated: one created by processing the signal as a time domain signal and one by processing the signal as a frequency domain signal. The two spectra have the same energy of noises, but different phases of noises. Thus, sensitivity of the magnetic resonance technique may be enhanced by averaging the two spectra.

Image Contrast

In the frequency swept excitation method, the magnetic field variation created by the applied gradient G can exceed other potential contributions (e.g., magnetic susceptibility differences and an inhomogeneous $B_0$) such that their effects are not perceivable in images. Images developed using the frequency swept excitation method are generally unaffected by transverse relaxation, provided $T_2 > 10$ dw (see FIG. 6). Under these conditions, the signal intensity depends only on $T_1$, and spin density ($M_0$) as:

$$S = M_0 \frac{1 - E_1^{SWIFT}}{1 - E_1^{SWIFT} \cos(\theta)} \sin(\theta). \tag{13}$$

For fixed TR, the maximum signal intensity is attained with optimum flip angle $\theta_{opt}$ which satisfies the equation $$\cos(\theta_{opt}) = E_1^{SWIFT}. \tag{14}$$

$T_1$ contrast can be evaluated from the derivative of the signal $$\frac{dS}{d(1/T_1)}.$$

For fixed TR, this derivative has a maximum at $\theta \approx 1.7\theta_{opt}$. A good compromise between sensitivity and contrast thus occurs in the range $\theta_{opt} < \theta < 1.7\theta_{opt}$, where $\theta_{opt}$ corresponds to a spin of interest which has the smallest $T_1$ value. For the case of $\theta < \theta_{opt}$, $T_1$-weighting becomes negligible, and image contrast is dictated mainly by spin density variations.

EXAMPLES

Computer simulations based on the classical Bloch equations can help to reveal the behavior of spins during the application of amplitude- and/or frequency-modulated pulses as taught herein.

FIG. 3 illustrates the oscillatory motion 30 of the magnetization components of a given isochromat having frequency ω. The isochromat excitation time in FIG. 3 is shown by the vertical dotted line 32. In FIG. 3, $M_x^{PM}(t)$ 34 presents the x-axis component of the transverse magnetization vector of the isochromat in a reference frame known as the phase-modulated (PM) frame, which rotates around the static magnetic field direction (z) with an angular velocity $\omega_c$ equal to the center frequency in the sweep range. $M_x^{FM}(t)$ 36 is the x-axis component in a frequency-modulated (FM) frame, which rotates synchronously with the (time-dependent) pulse frequency $\omega_{RF}(t)$. FIG. 3 also shows the absolute value of the transverse magnetiziation $M_{xy}(t)(\sqrt{M_x^2(t)+M_y^2(t)})$ 38. The PM frame rotates at a constant carrier frequency $\omega_c$, whereas the FM frame rotates in synchrony with the pulse frequency $\omega_{RF}(t)$. In the FM frame the orientation of $\omega_1(t)$ remains stationary during an frequency swept passage. The transformation between two frames is done by:

$$M_x^{FM}(t) + iM_y^{FM}(t) = (M_x^{PM})(t) + iM_y^{PM})\exp(-i\phi(t)t) \tag{15}$$

where $\phi(t) = (\omega_{RF}(t) - \omega_c)t + \pi/2$. The constant $\pi/2$ term arises because the rotated vector is perpendicular to the direction of the RF field. In FIG. 3, $M_x^{PM}(t)$ 34 presents the x-axis component of the transverse magnetization vector of the isochromat in phase-modulated (PM) reference frame, which rotates around the static magnetic field direction (z) with an angular velocity $\omega_c$) equal to the center frequency in the sweep range. $M_x^{FM}(t)$ 36 is the x-axis component in a frequency-modulated (FM) frame, which rotates synchronously with the (time-dependent) pulse frequency $\omega_{RF}(t)$.

Figure 6:
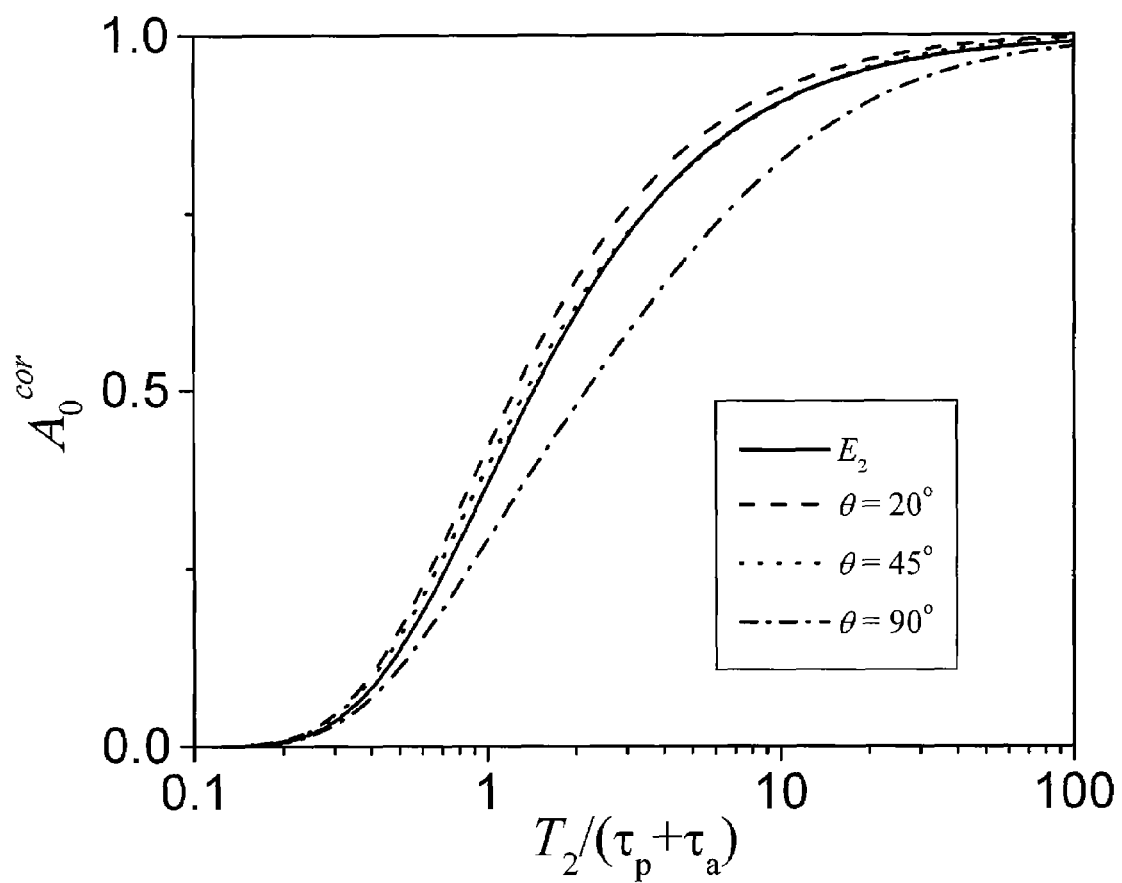
FIG. 6 illustrates simulated excitation performance of a pulse in the intermediate passage region in accordance with one embodiment.

As discussed previously, the frequency swept excitation method sequence has less stringent constraints than indicated by Eqs. (6a) and (6b). First, because the pulse is segmented, the average value of $\omega_1(t)$ scales inversely with $\tau_p$/dw. Second, according to simulation and experimental data, the correlation method works well up to a rotation angle near 90° before significantly violating the linearity condition of Eq. (6b). The frequency swept excitation method is not restricted to the rapid passage region by Eq. (6a). For example, the frequency swept excitation method may also be used in the intermediate passage, linear region, with the consequences of sacrificing signal-to-noise ratio (S/N) and resolution. To illustrate this point, FIG. 6 presents the excitation performance of the HS1 pulse in the intermediate passage region. The simulated parameter $A_0^{cor}$ is the normalized amplitude of the FID obtained by inverse FT of the correlated spectra. $A_0^{cor}$ is normalized to be equal to 1 for $T_2 \Rightarrow \infty$, $A_0^{cor}$ is plotted against $T_2/(\tau_p+\tau T_a)$ using different excitation flip angle θ (θ calculated for $T_2 \Rightarrow \infty$). The function $E_2 = \exp(-(\tau_p+\tau_a)/T_2)$ (solid line) well describes the dependencies. From this simulation, it can be seen that the limit of the $T_2$ sensitivity of the SWIFT sequence is $T_2 > \tau_p + \tau_a$~dw.

Figure 7:
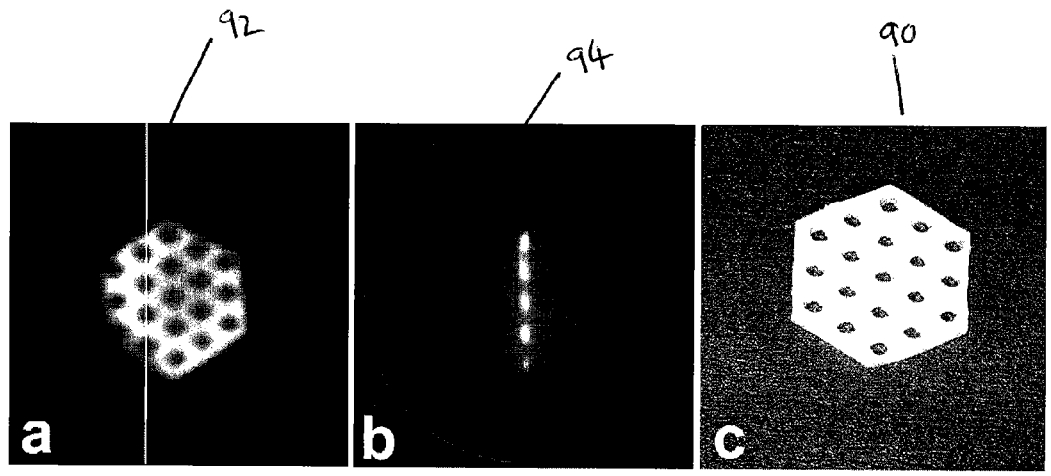
FIG. 7 illustrates images of slices of a 3D image of a thermoplastic object taken with the frequency swept method in accordance with one embodiment.
Figure 8:
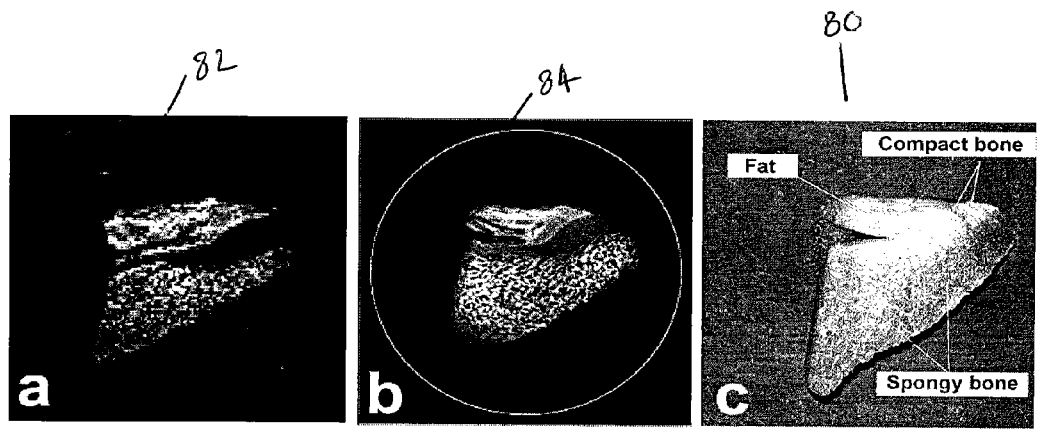
FIG. 8 illustrates comparative images of a specimen of bovine tibia images using a 2D gradient echo image and using the frequency swept method in accordance with one embodiment.

While the frequency swept excitation method may be used in a variety of applications, the method is demonstrated for imaging spins with extremely short $T_2$ values (FIGS. 7 and 8). The first test object, shown in FIG. 7, is thermoplastic 90, which is invisible by conventional MRI because the $T_2$ value is extremely short (~0.3 ms). As can be seen from FIG. 7, the frequency swept excitation method produced a highly resolved 3D image of the object. The images 92, 94 were obtained using a standard MRI scanner (4.7 T) which is not equipped with special software or hardware (e.g., solid state accessory).

Frequency swept excitation images of ex vivo bovine tibia 80 were also acquired to demonstrate the technique's sensitivity to short $T_2$ spins (FIG. 8). This image is compared to an image acquired using the shortest $T_E$ value (1.6 ms) that could be attained with a standard gradient-echo sequence. The cortical compact bone, which has $T_2 = 0.4$ ms, is not visible in the gradient-echo image 82 (FIG. 8), but is easily recognizable in the frequency swept excitation image 84 (FIG. 8).

These frequency swept excitation images were reconstructed using a standard 3D back-projection algorithm for 92, 94 of FIG. 7 and gridding for 84 of FIG. 8, with no additional processing (e.g., filtering) to remove subtle image intensity ripples and other minor artifacts.

Figure 9:
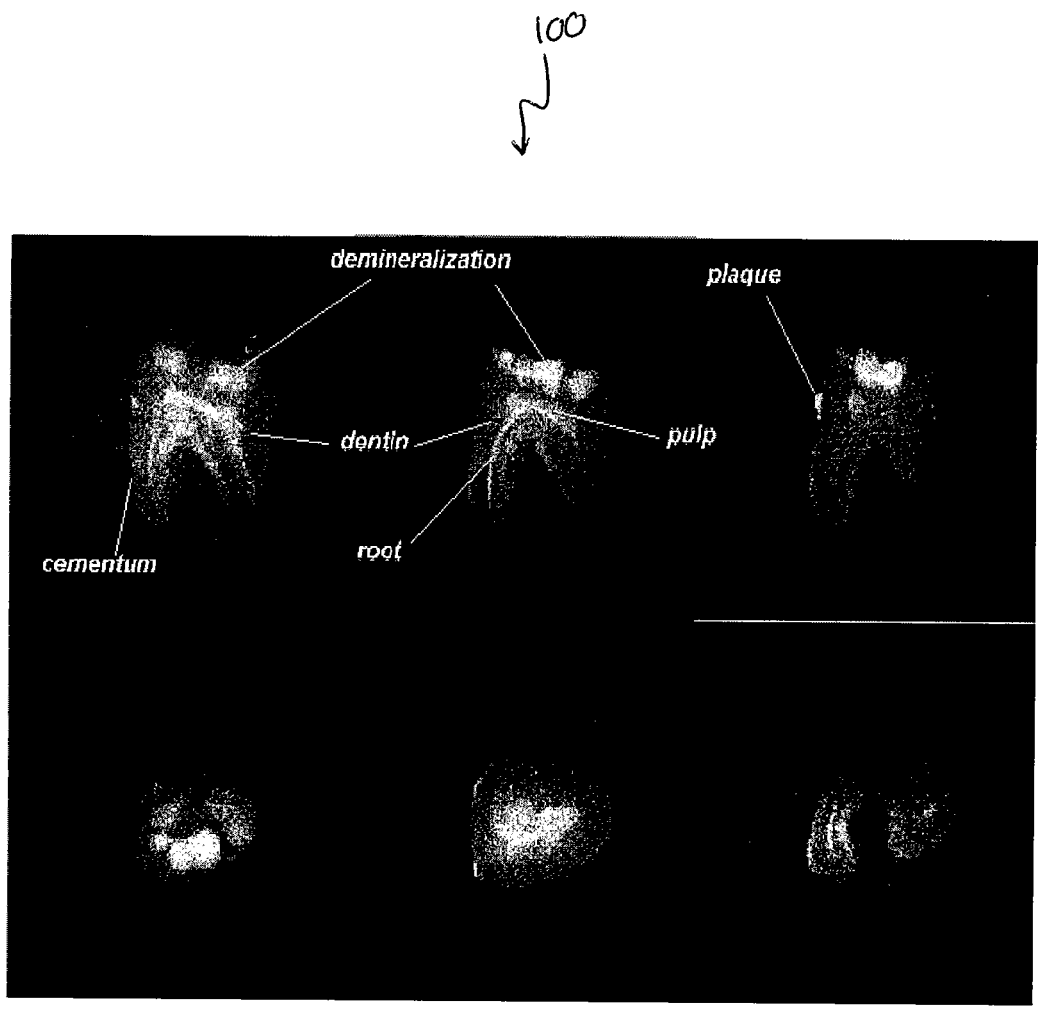
FIG. 9 illustrates images of tooth taken using the frequency swept method in accordance with one embodiment.

FIG. 9 illustrates images 100 of molar tooth decay made using the frequency swept excitation method. To create the images of FIG. 9, the following parameters were used: sw=62 kHz, 256×128×32, D=3 cm, 32 averages, total time=10 min, 4.7T. As may be appreciated, teeth are particularly hard to image using MRI techniques because most parts of the tooth (excluding, for example, the root) have very fast relaxing spins. While CW techniques can be used to image teeth, they typically take on the order of 10 hours. In contrast, using the frequency swept method, teeth were imaged in a total time of 10 minutes.

Although the invention has been described with reference to specific embodiments, persons skilled in the art will recognize that changes may be made in form and detail without departing from the spirit and scope of the invention.

What is claimed:

1. A method comprising:
    applying a sweeping frequency excitation having a duration, the sweeping frequency excitation being configured to sequentially excite isochromats having different resonant frequencies;
    acquiring a time domain signal during the duration, the time domain signal being based on evolution of the isochromats; and
    using the acquired time domain signal to create a magnetic resonance image.

2. The method of claim 1, further comprising applying a static magnetic field during applying the sweeping radio frequency excitation.

3. The method of claim 1, wherein acquiring a time domain signal continues after the duration.

4. The method of claim 1, wherein acquiring a time domain signal begins before the duration.

5. The method of claim 1, wherein applying the sweeping frequency excitation comprises applying a sweeping frequency excitation using a transmitter and wherein acquiring the time domain signal comprises detecting the signal on a receiver.

6. The method of claim 5, wherein the transmitter and receiver are decoupled.

7. The method of claim 1, further comprising generating a first spectra based on a correlation of a Fourier transform of the applied sweeping frequency excitation and a Fourier transform of the acquired time domain signal.

8. The method of claim 7, further comprising generating a second spectra based on a processing of the acquired time domain signal in a frequency domain and averaging the first and second spectra.

9. The method of claim 1, further comprising generating spectra based on deconvoluting the applied sweeping frequency excitation and the acquired time domain signal to generate a deconvoluted signal and Fourier transforming the deconvoluted signal.

10. The method of claim 9, further comprising generating a second spectra based on a processing of the acquired time domain signal in a frequency domain and averaging the first and second spectra.

11. The method of claim 1, further comprising applying a field gradient to create an image.

12. The method of claim 1, wherein applying the sweeping frequency excitation comprises applying a phase modulation.

13. The method of claim 1, wherein applying the sweeping frequency excitation comprises applying a frequency modulation.

14. The method of claim 1, wherein the time domain signal is based on evolution of magnetization of the isochromats.

15. The method of claim 1, further comprising processing the acquired time domain signal before using the acquired time domain signal to create a magnetic resonance image.

16. A method comprising:
    applying a sweeping frequency excitation having a duration, the sweeping frequency excitation being configured to sequentially excite isochromats having different resonant frequencies, wherein applying the sweeping frequency excitation includes applying a plurality of discrete excitation pulses;
    acquiring a time domain signal during the duration, the time domain signal being based on evolution of the isochromats, wherein acquiring the time domain signal includes sampling between excitation pulses; and
    using the acquired time domain signal to create a magnetic resonance image.

* * * * *